(12) United States Patent
Escala

(10) Patent No.: US 11,017,883 B1
(45) Date of Patent: May 25, 2021

(54) BLOCKCHAIN-BASED SYSTEMS AND METHODS FOR TRACKING DONATED GENETIC MATERIAL TRANSACTIONS

(71) Applicant: Eggschain, Inc., Austin, TX (US)

(72) Inventor: Wei Escala, Austin, TX (US)

(73) Assignee: EGGSCHAIN, INC., Austin, TX (US)

( * ) Notice: Subject to any disclaimer, the term of this patent is extended or adjusted under 35 U.S.C. 154(b) by 124 days.

(21) Appl. No.: 16/273,427

(22) Filed: Feb. 12, 2019

Related U.S. Application Data

(60) Provisional application No. 62/763,407, filed on Jun. 15, 2018, provisional application No. 62/764,644, filed on Aug. 15, 2018, provisional application No. 62/763,187, filed on Jun. 6, 2018.

(51) Int. Cl.
*H04L 9/06* (2006.01)
*G16B 50/00* (2019.01)
*G06F 16/903* (2019.01)

(52) U.S. Cl.
CPC .......... *G16B 50/00* (2019.02); *G06F 16/903* (2019.01); *H04L 9/0637* (2013.01); *H04L 2209/38* (2013.01)

(58) Field of Classification Search
CPC ...... G16B 50/00; G06F 16/903; H04L 9/0637
USPC .......................................................... 705/3
See application file for complete search history.

(56) References Cited

U.S. PATENT DOCUMENTS

| | | | |
|---|---|---|---|
| 2010/0191735 A1* | 7/2010 | Reiss | G16B 50/00 707/740 |
| 2017/0232300 A1* | 8/2017 | Tran | G06F 3/017 434/247 |
| 2017/0250972 A1* | 8/2017 | Ronda | H04L 9/3236 |

\* cited by examiner

*Primary Examiner* — Hiep V Nguyen
(74) *Attorney, Agent, or Firm* — Ulmer & Berne LLP

(57) ABSTRACT

Systems and methods are provided for tracking the provenance of donated genetic material using blockchain-based technologies. Immutable records of transactions associated with the donated genetic material are generated. These records can be utilized to create an audit trail for the genetic material.

15 Claims, 8 Drawing Sheets

BLOCKCHAIN-BASED SYSTEMS AND METHODS FOR TRACKING DONATED GENETIC MATERIAL TRANSACTIONS

CROSS-REFERENCE TO RELATED APPLICATIONS

The present application claims the benefit of provisional patent application Ser. No. 62/763,187 filed on Jun. 6, 2018, provisional patent application Ser. No. 62/763,407 filed on Jun. 15, 2018, and provisional patent application Ser. No. 62/764,644 filed on Aug. 15, 2018, the disclosures of which are each incorporated herein by reference in their entirety.

BACKGROUND

Demand for freezing eggs and other types of genetic material is growing rapidly. When a woman wants to know the status of her frozen eggs, however, her options are limited. While she may call or write the clinic/storage facility to request an update, there is no universal methodology. As a result, patients often do not know exactly where their eggs are stored. As genetic material is transported between storage vessels and storage locations, the chance of losing track of, or misidentifying the genetic material increases. Further, there is no trackable record of the estate plan relating to the eggs frozen after the woman becomes unable or unwilling to give birth with her eggs. Women and men also face moral and emotional dilemmas on what to do with leftover eggs/embryos, and there are very few resources available to help guide their decision-making.

BRIEF DESCRIPTION OF THE DRAWINGS

It is believed that certain embodiments will be better understood from the following description taken in conjunction with the accompanying drawings, in which like references indicate similar elements and in which.

DETAILED DESCRIPTION

Figure 1:
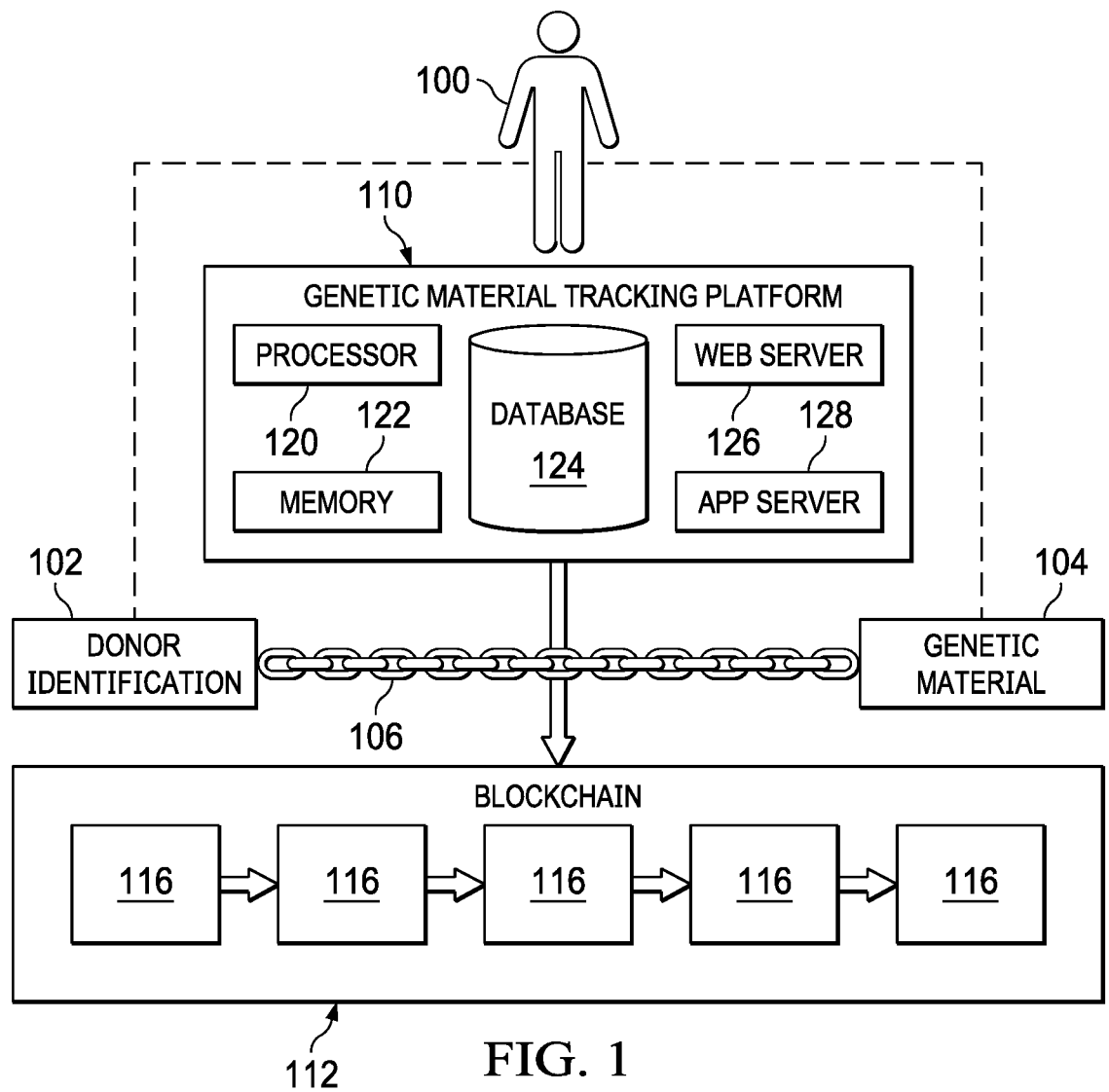
FIG. 1 schematically depicts a genetic material tracking platform that is configured to record and track the identity of a donor of genetic material in accordance with one non-limiting embodiment.

Various non-limiting embodiments of the present disclosure will now be described to provide an overall understanding of the principles of the structure, function, and use of systems and methods disclosed herein. One or more examples of these non-limiting embodiments are illustrated in the selected examples disclosed and described in detail with reference made to the figures in the accompanying drawings. Those of ordinary skill in the art will understand that systems and methods specifically described herein and illustrated in the accompanying drawings are non-limiting embodiments. The features illustrated or described in connection with one non-limiting embodiment may be combined with the features of other non-limiting embodiments. Such modifications and variations are intended to be included within the scope of the present disclosure.

The systems, apparatuses, devices, and methods disclosed herein are described in detail by way of examples and with reference to FIGS. 1-8. The examples discussed herein are examples only and are provided to assist in the explanation of the apparatuses, devices, systems and methods described herein. None of the features or components shown in the drawings or discussed below should be taken as mandatory for any specific implementation of any of these the apparatuses, devices, systems or methods unless specifically designated as mandatory. In addition, elements illustrated in the figures are not necessarily drawn to scale for simplicity and clarity of illustration. For ease of reading and clarity, certain components, modules, or methods may be described solely in connection with a specific figure. In this disclosure, any identification of specific techniques, arrangements, etc. are either related to a specific example presented or are merely a general description of such a technique, arrangement, etc. Identifications of specific details or examples are not intended to be, and should not be, construed as mandatory or limiting unless specifically designated as such. Any failure to specifically describe a combination or sub-combination of components should not be understood as an indication that any combination or sub-combination is not possible. It will be appreciated that modifications to disclosed and described examples, arrangements, configurations, components, elements, apparatuses, devices, systems, methods, etc. can be made and may be desired for a specific application. Also, for any methods described, regardless of whether the method is described in conjunction with a flow diagram, it should be understood that unless otherwise specified or required by context, any explicit or implicit ordering of steps performed in the execution of a method does not imply that those steps must be performed in the order presented but instead may be performed in a different order or in parallel.

Reference throughout the specification to "various embodiments," "some embodiments," "one embodiment," "some example embodiments," "one example embodiment," or "an embodiment" means that a particular feature, structure, or characteristic described in connection with any embodiment is included in at least one embodiment. Thus, appearances of the phrases "in various embodiments," "in some embodiments," "in one embodiment," "some example embodiments," "one example embodiment," or "in an embodiment" in places throughout the specification are not necessarily all referring to the same embodiment. Furthermore, the particular features, structures or characteristics may be combined in any suitable manner in one or more embodiments.

Throughout this disclosure, references to components or modules generally refer to items that logically can be grouped together to perform a function or group of related functions. Like reference numerals are generally intended to refer to the same or similar components. Components and modules can be implemented in software, hardware, or a combination of software and hardware.

The term "software" is used expansively to include not only executable code, for example machine-executable or machine-interpretable instructions, but also data structures, data stores and computing instructions stored in any suitable electronic format, including firmware, and embedded software. The terms "information" and "data" are used expansively and includes a wide variety of electronic information, including executable code; content such as text, video data, and audio data, among others; and various codes or flags. The terms "information," "data," and "content" are sometimes used interchangeably when permitted by context.

It should be noted that although for clarity and to aid in understanding, some examples discussed herein might describe specific features or functions as part of a specific component or module, or as occurring at a specific layer of a computing device (for example, a hardware layer, operating system layer, or application layer), those features or functions may be implemented as part of a different component or module or operated at a different layer of a communication protocol stack. Those of ordinary skill in the art will recognize that the systems, apparatuses, devices, and methods described herein can be applied to, or easily modified for use with, other types of equipment, can use other arrangements of computing systems such as client-server distributed systems, and can use other protocols, or operate at other layers in communication protocol stacks, than are described.

The systems and methods described herein generally provided for the tracking the provenance of donated genetic material using blockchain-based technologies. The systems and methods can also generate immutable records of transactions associated with the donated genetic material. These records can be used to create an audit trail for the genetic material, among other purposes. With specific regard to egg-freezing procedures, for example, the systems and methods disclosed herein can provide information to a donor of the eggs. For example, the frozen eggs received from the donor can be given a digital, trackable identity that is maintained by a genetic material tracking platform. The platform described herein can create permanent, immutable records that are recorded onto a blockchain usable to establish ownership, track ownership changes, track storage location, and so forth. Thus, platforms in accordance with the present disclosure can ensure frozen eggs, embryos, and other genetic material are properly tracked, monitored, and managed. In some embodiments, various types of users can interact with the genetic material tracking platform using a mobile computing devices, such as a smart phone or a tablet, or a variety of other types of computers, such as desktop computers, laptop computers, and the like.

FIG. 1 schematically depicts a genetic material tracking platform 110 that is configured to record and track the identity of a donor 100 from which genetic material 104 was obtained in accordance with one non-limiting embodiment. The genetic material 104 depicted in FIG. 1 is broadly representative of any type of genetic material that can be collected from, associated with, or otherwise donated by, the donor 100, such as an egg, an embryo, sperm, blood, tissue, stem cells, an organ, or other types of cells, matter, or material that can be preserved for later use. As is to be appreciated, the approaches to preserve the genetic material 104 can vary based on the type of material being preserved, but in some embodiments the genetic material 104 can be stored in liquid nitrogen tanks in a cryogenic facility, for example.

As shown in FIG. 1, the genetic material tracking platform 110 can establish a permanent association, schematically shown as link 106, between a donor identification 102 and the genetic material 104. In some embodiments, the identification of the donor identification 102 is a globally unique identifier (GUID) assigned to the donor 100, although this disclosure is not so limited. The link 106 between the donor 100 and the generic material 104 can be stored as an immutable record on a block of a blockchain 112.

As is to be appreciated by one skilled in the art, the blockchain 112 is formed by a series of blocks 116, which each block 116 containing a cryptographic hash of the previous block, a timestamp, and transaction data (generally represented as a Merkle tree root hash). The blockchain 112 is a distributed ledger that can record transactions efficiently and in a verifiable and permanent way. By design, the blockchain 112 is resistant to modification of the data. The blockchain 112 can be managed by a peer-to-peer network collectively adhering to a protocol for inter-node communication and validating new blocks. In some embodiments, the blockchain 112 is implemented on Ethereum, which is a distributed public blockchain network. Once recorded, data in any given block 116 cannot be altered retroactively without alteration of all subsequent blocks 116, which requires consensus of the network majority. Therefore, in accordance with the present disclosure, once the link 106 between the genetic material 104 and the donor identification 102 is recorded as a block 116 on the blockchain 112 via API calls or other suitable methods, a permanent and immutable record is created.

The genetic material tracking platform 110 may be embodied as any type of server or computing device or computer devices that are capable of processing, communicating, storing, maintaining, and transferring data. For example, the genetic material tracking platform 110 may be embodied as a server, a microcomputer, a minicomputer, a mainframe, a desktop computer, a laptop computer, a mobile computing device, a handheld computer, a smart phone, a tablet computer, a personal digital assistant, a telephony device, a custom chip, an embedded processing device, or other computing device and/or suitable programmable device. In some embodiments, the genetic material tracking platform 110 may be embodied as a computing device integrated with other systems or subsystems.

In the illustrative embodiment of FIG. 1, the genetic material tracking platform 110 includes a processor 120 and a memory unit 122. Data used by the genetic material tracking platform 110 can be from various data sources, such as a database 124, which can store data associated with the donor 100, along with data associated with clinics, laboratories, doctor's offices, among other information. The data stored in the database 124 can be stored in a non-volatile computer memory, such as a hard disk drive, a read only memory (e.g., a ROM IC), or other types of non-volatile memory. In some embodiments, the database 124 can be stored on a remote electronic computer system, such as cloud-based storage, for example. As it to be appreciated, a variety of other databases, or other types of memory storage structures, can be utilized or otherwise associated with the genetic material tracking platform 110. As such, the data sources utilized by the genetic material tracking platform 110 may be embodied as any type of device or devices configured for short-term or long-term storage of data such as, for example, memory devices and circuits, memory cards, hard disk drives, solid-state drives, or other data storage devices. For example, in some embodiments, the data sources include storage media such as a storage device that can be configured to have multiple modules, such as magnetic disk drives, floppy drives, tape drives, hard drives, optical drives and media, magneto-optical drives and media, compact disk drives, Compact Disk Read Only Memory (CD-ROM), Compact Disk Recordable (CD-R), Compact Disk Rewriteable (CD-RW), a suitable type of Digital Versatile Disk (DVD) or Blu-Ray disk, and so forth. Storage media such as flash drives, solid state hard drives, redundant array of individual disks (RAID), virtual drives, networked drives and other memory means including storage media on the processor 120 or the memory unit 122, are also contemplated as storage devices. It should be appreciated that such memory can be internal or external with respect to operation of the disclosed embodiments. It should also be appreciated that certain portions of the processes described herein can be performed using instructions stored on a computer-readable medium or media that direct or otherwise instruct a computer system to perform the process steps. Non-transitory computer-readable media, as used herein, comprises all computer-readable media except for transitory, propagating signals.

The genetic material tracking platform 110 can include several computer servers and databases. For example, the genetic material tracking platform 110 can include one or more web servers 126, application servers 128, and/or any other type of servers. For convenience, only one web server 126 and one application server 128 are shown in FIG. 1, although it should be recognized that the disclosure is not so limited. The servers 128, 126 can comprise processors (e.g., CPUs), memory units (e.g., RAM, ROM), non-volatile storage systems (e.g., hard disk drive systems), etc. The servers 128, 126 can utilize operating systems, such as Solaris, Linux, or Windows Server operating systems, for example.

The web server 126 can provide a graphical web user interface through which various users of the system can interact with the genetic material tracking platform 110. The web server 126 can accept requests, such as HTTP requests, from clients and serve the client's responses, such as HTTP responses, along with optional data content, such as web pages (e.g., HTML documents) and linked objects (such as images, video, and so forth). The application server 128 can provide a user interface for users who do not communicate with the genetic material tracking platform 110 using a web browser. Such users can have special software installed on computing devices that allows them to communicate with the application server 128 via a communications network, such as communications network 230 described below with regard to FIG. 2.

Of course, the genetic material tracking platform 110 may include other or additional components, such as those commonly found in a server and/or computer (e.g., various input/output devices), in other embodiments. Additionally, in some embodiments, one or more of the illustrative components may be incorporated in, or otherwise form a portion of, another component. For example, the memory unit 122, or portions thereof, may be incorporated in the processor 120 in some embodiments. Furthermore, it should be appreciated that the genetic material tracking platform 110 may include other components, sub-components, and devices commonly found in a computer and/or computing device, which are not illustrated in FIG. 1 for clarity of the description.

The processor 120 may be embodied as any type of processor capable of performing the functions described herein. For example, the processor 120 may be embodied as a single or multi-core processor, a digital signal processor, microcontroller, a general purpose central processing unit (CPU), a reduced instruction set computer (RISC) processor, a processor having a pipeline, a complex instruction set computer (CISC) processor, an application specific integrated circuit (ASIC), a programmable logic device (PLD), a field programmable gate array (FPGA), or other processor or processing/controlling circuit or controller.

The memory unit 122 may be embodied as any type of volatile or non-volatile memory or data storage capable of performing the functions described herein. For example, the memory unit 122 may be embodied as read only memory (ROM), random access memory (RAM), cache memory associated with the processor 120, or other memories such as dynamic RAM (DRAM), static ram (SRAM), programmable ROM (PROM), electrically erasable PROM (EEPROM), flash memory, a removable memory card or disk, a solid state drive, and so forth. In operation, the memory unit 122 may store various data and software used during operation of the genetic material tracking platform 110 such as operating systems, applications, programs, libraries, and drivers.

Additionally, in some embodiments, the genetic material tracking platform 110 can further include one or more peripheral devices (not shown). Such peripheral devices can include any type of peripheral device commonly found in a computing device such as additional data storage, speakers, a hardware keyboard, a keypad, a gesture or graphical input device, a motion input device, a touchscreen interface, one or more displays, an audio unit, a voice recognition unit, a vibratory device, a computer mouse, a peripheral communication device, and any other suitable user interface, input/output device, and/or other peripheral device.

Figure 2:
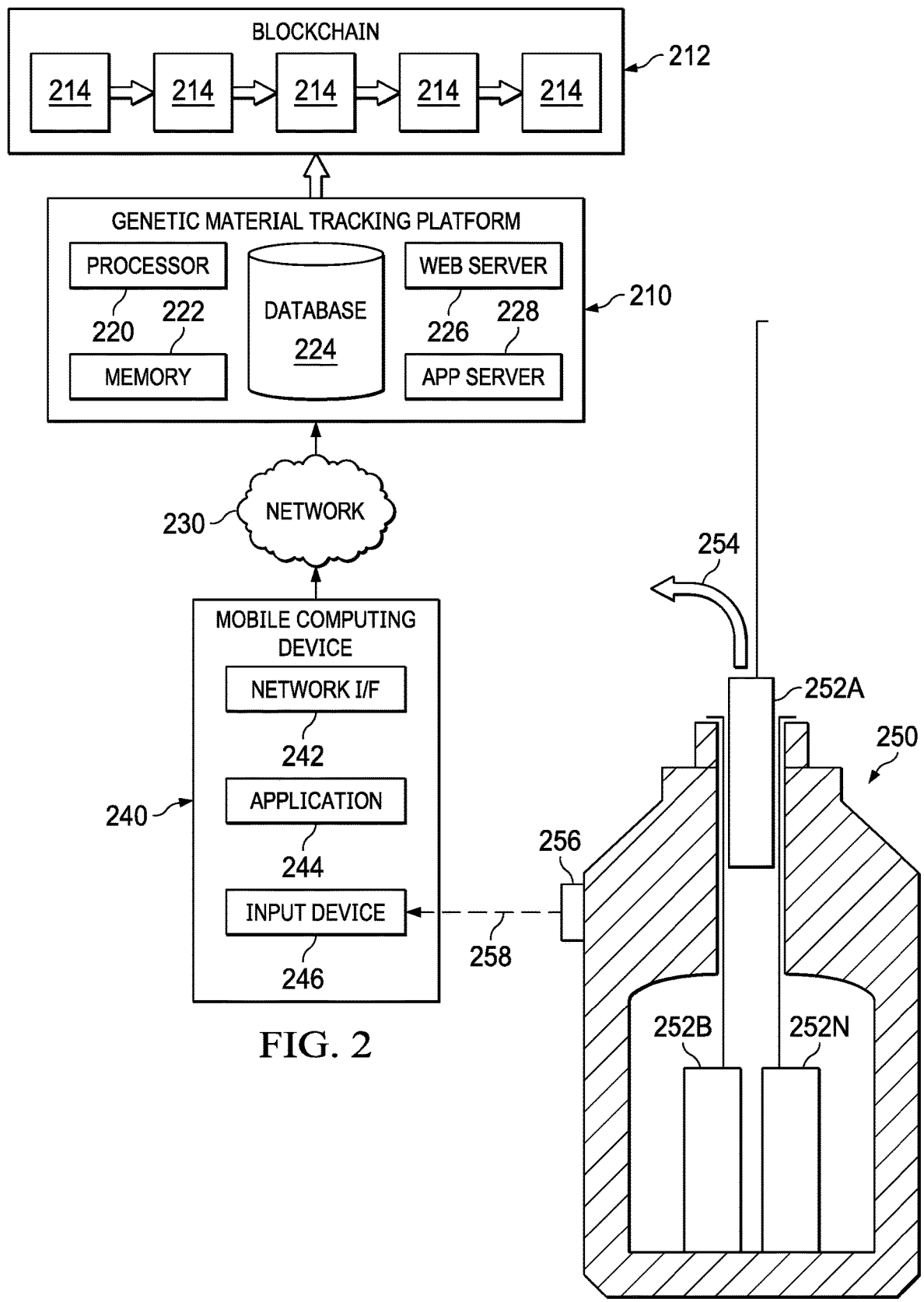
FIG. 2 schematically shows the tracking of genetic material by a genetic material tracking platform in accordance with one non-limiting embodiment.

Referring now to FIG. 2, a genetic material tracking platform 210 is schematically shown tracking a genetic material transaction involving a vessel 250 for storing genetic material. Similar to FIG. 1, the genetic material tracking platform 210 can have a processor 220 and a memory unit 222. The genetic material tracking platform 210 can also have a database 224, a web server 226, and an app server 228. The genetic material tracking platform 210 can be in communication with a mobile computing device 240 via a communications network 230. The communications network 230 can be embodied as any number of various wired and/or wireless communication networks. For example, the communications network 230 can be embodied as or otherwise include a local area network (LAN), a wide area network (WAN), a cellular network, or a publicly-accessible, global network such as the Internet.

The mobile computing device 240 can be operated by any suitable user, such as a clinician, doctor, nurse, and so forth. The mobile computing device 240 can be, without limitation, a smart phone, tablet, wearable computer, or other type of device capable of network communication via a network interface 242. The mobile computing device 240 can execute an application 244 associated with the genetic material tracking platform 210. The application 244 can be a specialized application downloaded and installed on the mobile computing device 240. The application 244 can also be a web browser or any other application that allows data communication between the mobile computing device 240 and the genetic material tracking platform 210.

A cross-sectional view of the example vessel 250 is shown. While vessel 250 is a cryogenic-type tank, it is to be appreciated that the systems and methods described herein are applicable to a number of different vessel types and vessel sizes. In FIG. 2, genetic material (such as genetic material 104 shown in FIG. 104) can be stored in canisters 252A-N. In some embodiments, the vessel 250 can be configured to store genetic material from a single donor. In some embodiments, the vessel 250 can be configured to store genetic material from numerous different donors. The vessel can be associated with a vessel identifier 256, which, for the purposes of illustration, is schematically shown to be attached to an outer surface of the vessel 250. The vessel identifier 256 can be any device that is capable of conveying information. In this regard, the vessel identifier 256 can be a human readable code that is printed or otherwise affixed to the vessel 250. Additionally or alternatively the vessel identifier 256 can be a scannable code, such as a barcode or a QR code, for example. Such scannable codes can be scanned by a camera of the mobile computing device 240, or other type of scanner or reader. Additionally or alternatively the vessel identifier 256 can be configured to convey information via a near field communication protocol, such as via a Bluetooth® protocol, for example. Additionally or alternatively the vessel identifier 256 can be configured to convey information when polled by a reader, such as an RFID circuit. In any event, when genetic material is deposited into the vessel 250 or removed from the vessel 250, the vessel identifier 256 can be used to convey vessel identification information to a mobile computing device 240.

In accordance with various embodiments, when a user removes genetic material from the vessel 250, as schematically shown by arrow 254, the user can interface with the application 244 executing on the mobile computing device 240 to log, document, or otherwise account for the transaction. In this regard, for example, the user can obtain information from the vessel identifier 256 using an input device 246 of the mobile computing device 240, such as a keypad, a camera, scanner, an antenna, and so forth. The user can also interact with the application 244 via an interface to provide additional information, such as the identification of the genetic material removed from the vessel 250, among other details. The form of the identification of the genetic material entered into the application 244 can vary, but in some embodiments, the identification includes the donor's name and the donor's doctor's name. However, this disclosure is not so limited.

The mobile computing device 240 can transmit the information associated with the genetic material transaction to the genetic material tracking platform 210. Once received by the genetic material tracking platform 210 a record of the transaction can be created that includes transactional details such as, for example, the vessel identifier 256, the time/date of transaction, the user, the genetic material involved, and so forth. The record can then be added as a block 214 of a blockchain 212, as described above with regard to FIG. 1. As is to be appreciated, in some embodiments, the record can be a database record maintained by the database 224 of the genetic material tracking platform 210 and the record added to the blockchain 210 can effectively be a pointer to the database record, thereby allowing for subsequent retrieval of the information in the database record. As such, in accordance with the present disclosure, all transactions of genetic material associated with the vessel 250 can be tracked and logged by the genetic material tracking platform 210 and recorded as blocks 214 on the blockchain 212 to create permanent and immutable records of each transactions.

Figure 3:
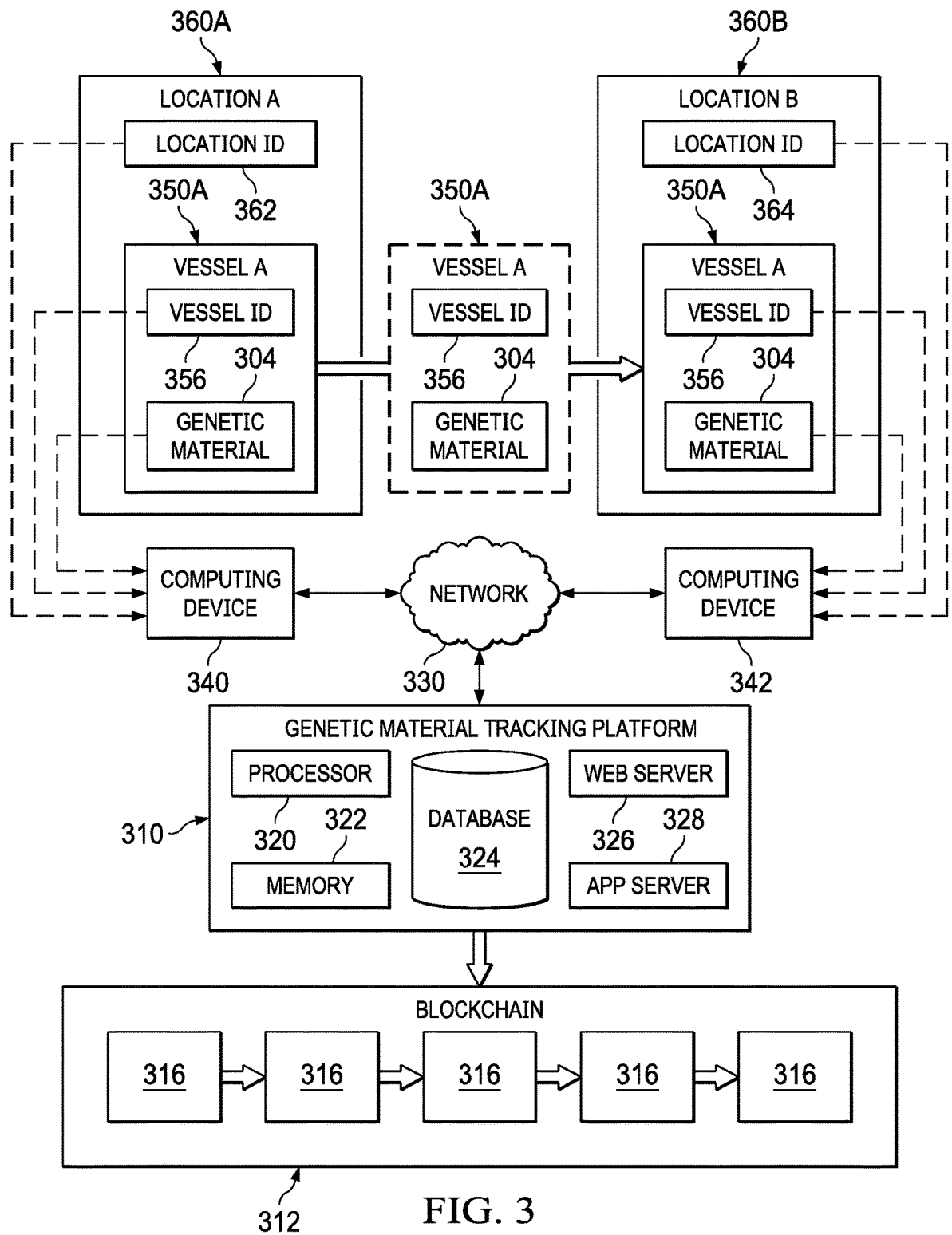
FIGS. 3-4 schematically show the movement of genetic material between various locations and/or various vessels being tracked and recorded by a genetic material tracking platform in accordance with one non-limiting embodiment.
Figure 4:
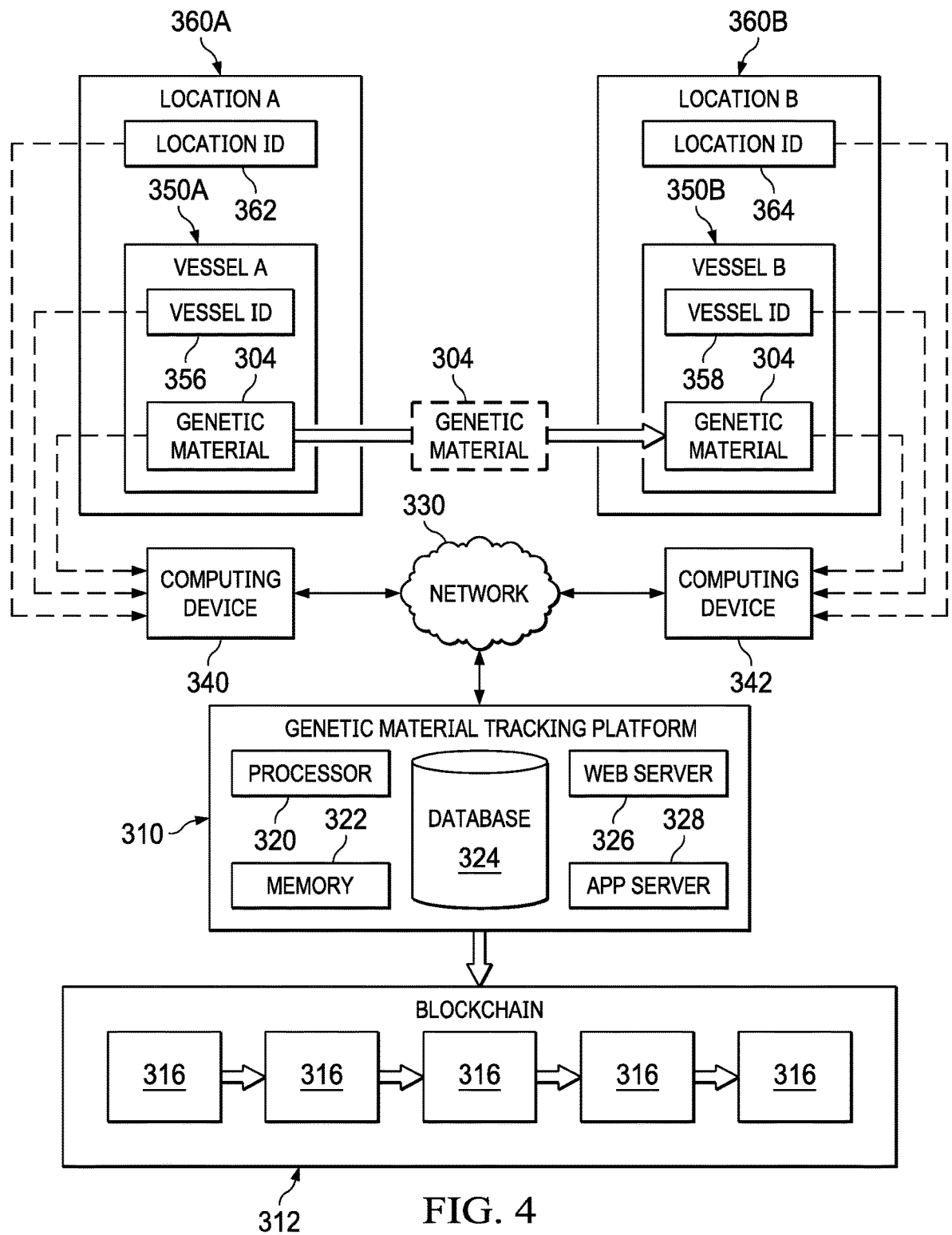

Subsequent to the collection of genetic material form a donor, the genetic material may be transported between labs, clinics, or other types of storage facilities. As schematically shown in FIGS. 3 and 4, the systems and methods described herein can utilize a genetic material tracking platform 310 to track and record the movement of genetic material between various locations and/or various vessels as blocks 316 on a blockchain 312. Similar to FIG. 1, the genetic material tracking platform 310 can have a processor 320 and a memory unit 322. The genetic material tracking platform 310 can also have a database 324, a web server 326, and an app server 328.

Referring first to FIG. 3, genetic material is shown stored within a vessel 350A, which has a vessel identifier 356. The vessel 350A is shown being stored at a location 360A. In this embodiment, the location 360A has a location identifier 362 that can be uniquely associated with the location 360A. The granularity of the information provided by the location identifier 362 can vary, but in some embodiments the location identifier 362 is associated with the address of the facility, a storage area of a storage facility, or a section of a storage area of a storage facility. As schematically shown in FIG. 3, information is provided to a computing device 340 to create a record indicating that genetic material 304 is contained within vessel 350A which is initially located at the location 360A. This information can be provided through a communications network 330 by the computing device 340 to the genetic material tracking platform 310. The computing device 340 can be any suitable device, such as a laptop, a desktop, a mobile computing device, a wearable device, a tablet computer, and so forth. The genetic material tracking platform 310 can log information associated with the location of the genetic material 304 onto the blockchain 312, as described above.

As is illustrated in FIG. 3, the vessel 350A is shown being moved from the location 360A to location 360B. In this embodiment, the location 360B has a location identifier 364 that can be uniquely associated with the location 360B. As schematically shown in FIG. 3, information can be provided to computing device 342 to create a record indicating that the genetic material 304 contained within the vessel 350A has been moved to the location 360B. This information can be provided through the communications network 330 by the computing device 340 to the genetic material tracking platform 310. The computing device 342 can be any suitable device, such as a laptop, a desktop, a mobile computing device, a wearable device, a tablet computer, and so forth. The genetic material tracking platform 310 can log information associated with the new location of the genetic material 304 onto the blockchain 312.

Referring now to FIG. 4, another example genetic material transaction is schematically illustrated. In this transaction, the genetic material 304 is transferred between two different vessels 350A, 350B, each of which is physically located in different locations 360A, 360B. The two different locations 360A, 360B can be separate storage facilities, or can be two different locations within a single storage facility, for example. As shown in FIG. 4, information is provided to the computing device 340 to create a record indicating that the genetic material 304 is contained within the vessel 350A, which is initially located at the location 360A. The genetic material 304 is then moved from location 360A to location 360B. As schematically shown in FIG. 4, information can be provided to the computing device 342 to create a record indicating that the genetic material 304 has been moved to vessel 350B, which is located at location 360B. This information can be provided through the communications network 330 by the computing device 340 to the genetic material tracking platform 310. The genetic material tracking platform 310 can log information associated with the new location of the genetic material 304 onto the blockchain 312.

While FIGS. 3 and 4 schematically depict the combined use of location identifiers and vessel identifiers, this disclosure is not so limited. In some embodiments, for example, the genetic material tracking platform may only utilize location identifiers or vessel identifiers. Or in some embodiments, other forms of identifiers, such as canister identifiers, or tracking devices can be used by the genetic material tracking platform to document and record genetic material transactions.

The systems and methods described herein can also be utilized to generate an audit log for genetic material transactions. Generally, audit logs in accordance with the present disclosure can be based on the transactions recorded on a blockchain by a genetic material tracking platform. The audit log can therefore include details for each transaction involving genetic material being tracked by a genetic material tracking platform. In this regard, an audit log can include donor identification information, time/date of genetic material collection, date of freezing, dates at various storage facilities, and any other information that can be logged, tracked, or documented by a genetic material tracking platform.

Figure 5:
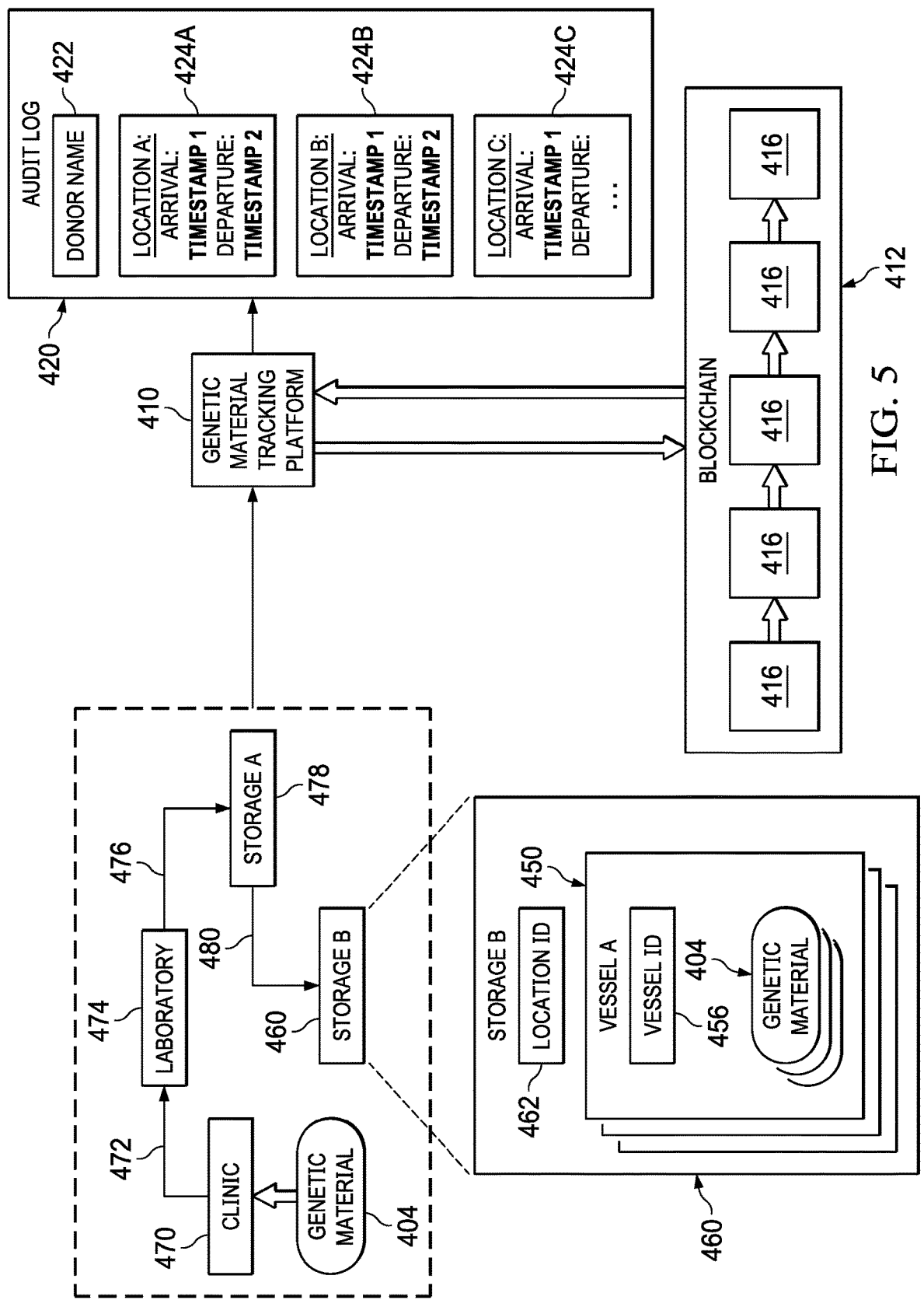
FIG. 5 schematically depicts the generation of an example audit log by a genetic material tracking platform.

FIG. 5 schematically depicts the generation of an audit log 420 for genetic material 404 by an example genetic material tracking platform 410. In the illustrated example, the genetic material 404 is collected at a clinic 470. This event can be logged on a blockchain 412 by the genetic material tracking platform 410. As a result of transaction 472, the genetic material 404 is transferred to laboratory 474. This event can be logged on the blockchain 412 by the genetic material tracking platform 410. As a result of transaction 476, the genetic material 404 is next transferred to a storage center 478. This event can be logged on the blockchain 412 by the genetic material tracking platform 410. As a result of transaction 480, the genetic material 404 is finally transferred to another storage center 460. Similar to the embodiments described above with regard to FIGS. 3-4, the genetic material 404 can be stored within a vessel 450 having a vessel identifier 456. The storage center 460 can also have a location identifier 462.

In order to create the audit log 420, the genetic material tracking platform 410 can poll the blockchain 412 to retrieve the transactional information. The audit log 420 is schematically shown in FIG. 5 to include donor identification information 422, as well as information regarding each location 424A-C at which the genetic material 404 was stored. As illustrated, the audit log 420 can include, for example, timestamps indicating when the genetic material 404 arrived/departed a location. As is to be appreciated, the audit log 420 can include a wide array of information that is tracked by the genetic material tracking platform 410, such as vessel identifiers, location identifier, canister identifies, and so forth. Thus, in accordance with the present disclosure, a verifiable chain of custody from the time of donation to the present point in time can be generated by a genetic material tracking platform and provided to a user.

Figure 6:
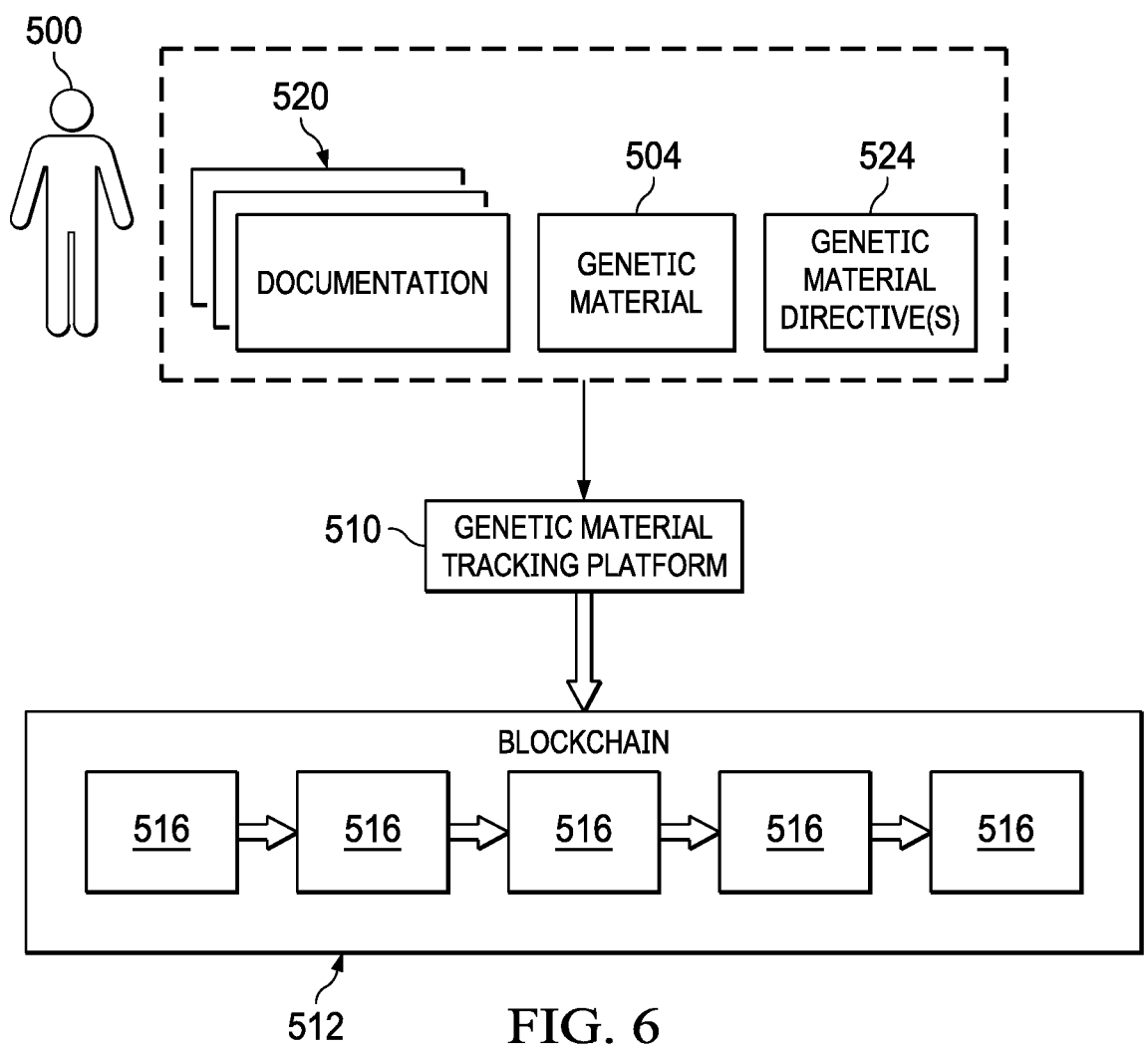
FIG. 6 depicts additional documentation that can be provided by a donor and that can be associated with genetic material in accordance with one non-limiting embodiment.

FIG. 6 depicts additional documentation that can be provided by a donor 500 and that can be associated with genetic material 504. As is known in the art, certain types of procedures may require a donor to provide various types of forms, certifications, documents, medical reports, and/or other types of records, which are collectively referred to herein as documentation 520. Such documentation 520 can be uploaded to a genetic material tracking platform 510 using any suitable technique and stored in a database or other type of storage vehicle. The documentation 520 received from the donor 500 can be associated with the donor 500 and the genetic material 504 and recorded onto a block 516 of a blockchain 512 to create an immutable and permanent record. The documentation 520 can be retrieved at a later point in time for any of a variety of reasons, such as to resolve disputes, prove consent, among a variety of other reasons.

Further, in some embodiments, genetic material directives 524 can be collected from the donor 500. Genetic material directives 524, sometimes referred to as estate plans, can indicate what should happen to the genetic material 504 in the event certain situations occur, such as the donor 500 dies, gets divorced, or becomes incapacitated, among any number of other scenarios. The genetic material tracking platform 510 can associate the genetic material 504 with the genetic material directives 524 and record the association on the blockchain 512. Thus, the genetic material directives 524 can be retrieved by the genetic material tracking platform 510 should certain scenarios come to fruition.

In some embodiments, the genetic material directives 524 are implemented as smart contracts that are stored on the blockchain 512 and that cause the execution of certain actions when certain conditions exist. For example, in the event of a death of a donor 500, the ownership of the genetic material 504 can be transferred to a spouse of the donor 500.

Figure 7:
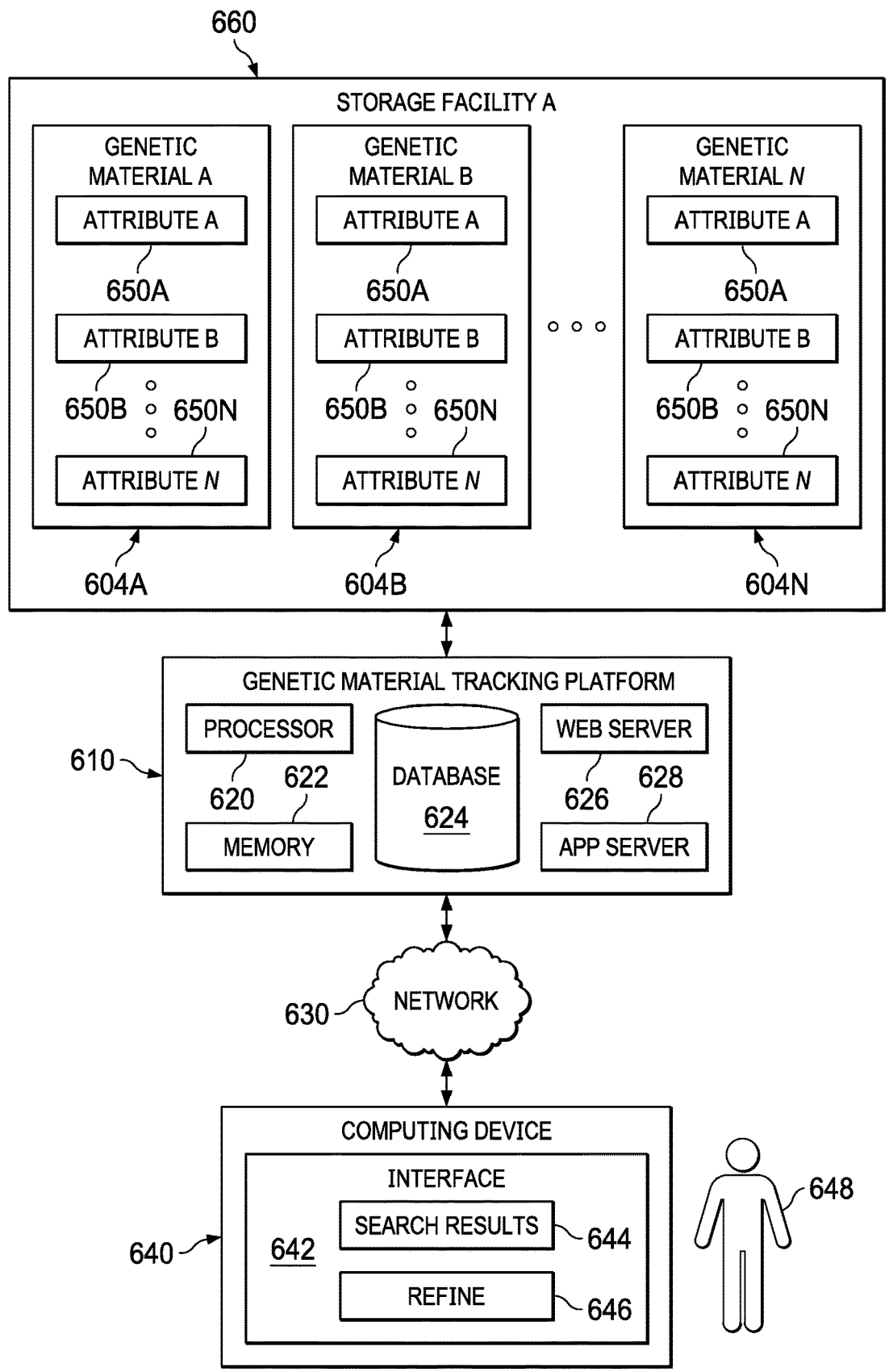
FIGS. 7-8 depict a genetic material tracking platform providing an online repository for displaying information regarding genetic material deposits that are available for purchase or other types of acquisition.

FIG. 7 depicts a genetic material tracking platform 610 providing an online repository for displaying information regarding genetic material deposits that are available for purchase or other types of acquisition. Similar to the previously described embodiments, the genetic material tracking platform 610 can have a processor 620 and a memory unit 622. The genetic material tracking platform 610 can also have a database 624, a web server 626, and an app server 628. A user 648 can remotely access an online repository provided by the genetic material tracking platform 610 via computing device 640. The computing device 640 can be any suitable type of device having a network connection, such as a smartphone, laptop, desktop, tablet, and so forth.

The genetic material tracking platform 610 can store attributes 650A-N associated with genetic material 604A-N that is stored at storage facility 660. While one storage facility 660 is illustrated in in FIG. 7, it is to be appreciated that the genetic material tracking platform 610 can store attributes associated with genetic material stored at a plurality of different storage facilities. The types of attributes 650A-N can vary, and certain genetic material deposits may have more or less attributes than others. Non-limiting example types of attributes that may be associated with one of the genetic material 604A-N include location information, donor information, embryo freeze date, embryo donation date, number of embryos donated, embryo freezing technique, number of embryos remaining, donor age (female), donor age (male), date of birth for sperm source, height of sperm source, weight of sperm source, drug allergies of sperm source, race of sperm source, ethnic background of sperm source, handedness of sperm source, hair information of sperm source, skin information of sperm source, body information of sperm source, medical history of sperm source, educational information of sperm source, occupational information of sperm source, musical ability information of sperm source, artistic ability of sperm source, date of birth for oocyte source, height of oocyte source, weight of oocyte source, drug allergies of oocyte source, race of oocyte source, ethnic background of oocyte source, handedness of oocyte source, hair information of oocyte source, skin information of oocyte source, body information of oocyte source, medical history of oocyte source, educational information of oocyte source, occupational information of oocyte source, musical ability information of oocyte source, artistic ability of oocyte source, child medical conditions, and child developmental conditions.

The user 648 can access the online repository via the computing device 640 having an interface 642. The user 648 can provide queries to the genetic material tracking platform 610, and search results 644 can be displayed in response to the query entered by the user 648. The query can identify one or more attributes and the genetic material tracking platform 610. The user 648 can refine the search results 644, as shown by refinement option 646, to further enhance the search results 644. Upon finding a particular genetic material 604A-N of interest, the genetic material tracking platform 610 can provide contact information to the user 648 or otherwise assist with the transfer of the selected genetic material 604A-N to the user 648.

Figure 8:
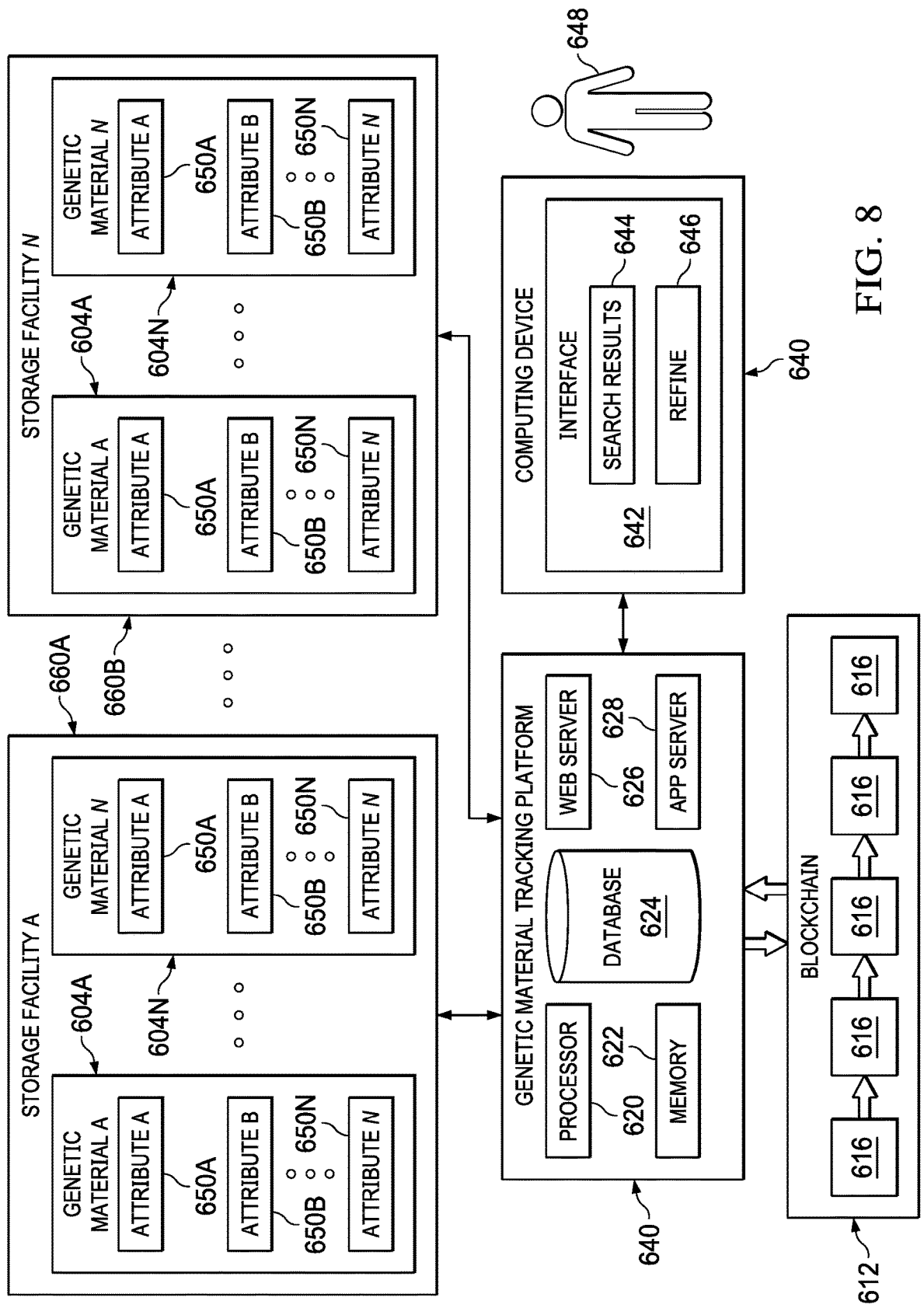

FIG. 8 schematically shows another embodiment in which information used by the genetic material tracking platform 610 is retrieved from blocks 616 of a blockchain 612. As such, the provenance of some or all of the genetic material 604A-N that is stored at the storage facilities 660A-B can be tracked and logged on the blockchain 612. The user 648 shown in FIG. 8 can therefore receive audit logs (similar to audio logs 420, for example), confirming the chain of custody of the selected genetic material 604A-N, or otherwise confirming the donor information from blockchain-based records.

It is to be understood that the figures and descriptions of the present invention have been simplified to illustrate elements that are relevant for a clear understanding of the present invention, while eliminating, for purposes of clarity, other elements. Those of ordinary skill in the art will recognize, however, that these sorts of focused discussions would not facilitate a better understanding of the present invention, and therefore, a more detailed description of such elements is not provided herein.

Any element expressed herein as a means for performing a specified function is intended to encompass any way of performing that function including, for example, a combination of elements that performs that function. Furthermore the invention, as may be defined by such means-plus-function claims, resides in the fact that the functionalities provided by the various recited means are combined and brought together in a manner as defined by the appended claims. Therefore, any means that can provide such functionalities may be considered equivalents to the means shown herein. Moreover, the processes associated with the present embodiments may be executed by programmable equipment, such as computers. Software or other sets of instructions that may be employed to cause programmable equipment to execute the processes may be stored in any storage device, such as, for example, a computer system (non-volatile) memory, an optical disk, magnetic tape, or magnetic disk. Furthermore, some of the processes may be programmed when the computer system is manufactured or via a computer-readable memory medium.

It can also be appreciated that certain process aspects described herein may be performed using instructions stored on a computer-readable memory medium or media that direct a computer or computer system to perform process steps. A computer-readable medium may include, for example, memory devices such as diskettes, compact discs of both read-only and read/write varieties, optical disk drives, and hard disk drives. A non-transitory computer-readable medium may also include memory storage that may be physical, virtual, permanent, temporary, semi-permanent and/or semi-temporary.

These and other embodiments of the systems and methods can be used as would be recognized by those skilled in the art. The above descriptions of various systems and methods are intended to illustrate specific examples and describe certain ways of making and using the systems disclosed and described here. These descriptions are neither intended to be nor should be taken as an exhaustive list of the possible ways in which these systems can be made and used. A number of modifications, including substitutions of systems between or among examples and variations among combinations can be made. Those modifications and variations should be apparent to those of ordinary skill in this area after having read this disclosure.

What is claimed is:

1. A method of genetic material provenance tracking, the method comprising:
   (a) assigning, by a genetic material tracking platform, a globally unique identifier to a donor;
   (b) subsequent to the collection of genetic material from the donor, linking, by the genetic material tracking platform, the genetic material collected from the donor with the globally unique identifier of the donor by:
      (i) storing, by the genetic material tracking platform, a private record on a database, wherein the private record includes an identity of the donor and the globally unique identifier; and
      (ii) storing, by the genetic material tracking platform, an immutable record on a blockchain, wherein the immutable record includes a cryptographic hash that is based on a preceding immutable record, and a pointer that corresponds to the private record, wherein the pointer is usable to determine a correspondence between the private record and the immutable record;
   (c) coupling a vessel identifier to a vessel containing the genetic material, wherein the vessel identifier comprises the globally unique identifier;
   (d) receiving, by the genetic material tracking platform, the globally unique identifier from a scanner at a first location and storing a first immutable location record on the blockchain that associates the globally unique identifier with a first location identifier that describes the first location;
   (e) after the vessel is moved from the first location to a second location, receiving, by the genetic material tracking platform, the globally unique identifier from a scanner at the second location and storing a second immutable location record on the blockchain that associates the globally unique identifier with a second location identifier that describes the second location, wherein each of the first location and the second location include an address of a facility, a storage area of the facility, and a section of the storage area;
   (f) receiving, by the genetic material tracking platform, one or more documentary records from the donor and storing a set of immutable documentary records on the blockchain that associate the globally unique identifier with the one or more documentary records;
   (g) creating an audit log that describes a chain of custody for the genetic material based on:
      (i) one or more private records from the database that are associated with the genetic material;
      (ii) one or more immutable records from the blockchain that are associated, by pointers, with the one or more private records;
      (iii) a verification of a plurality of cryptographic hashes from the blockchain, including the cryptographic hash;

(iv) a plurality of immutable location records that describe a current location and any past locations of the vessel; and
(v) the one or more documentary records.

2. The method of claim 1, wherein the genetic material is any of an egg, an embryo, sperm, blood, tissue, stem cells, a genome, DNA, RNA, nucleic acid, and an organ.

3. The method of claim 1, wherein the one or more documentary records comprise an estate plan for any of an egg, an embryo, a genome, DNA, RNA, nucleic acid, or sperm.

4. The method of claim 1, wherein the blockchain is any of a public blockchain, a private blockchain, or a combination of a public and private blockchain.

5. The method of claim 1, wherein the private record indicates a current owner of the genetic material and the chain of custody describes the current owner and any past owners of the genetic material, further comprising, by the genetic material tracking platform:
   (a) receiving an ownership change indicating a change in ownership of the genetic material;
   (b) updating the current owner of the private record based on the ownership change; and
   (c) storing a subsequent immutable record on the blockchain, wherein the subsequent immutable record includes a second pointer that corresponds to the updated private record.

6. The method of claim 5, further comprising associating a smart contract with the genetic material that is configured to:
   (a) receive input indicating the occurrence of a condition; and
   (b) provide the ownership change to the genetic material tracking platform in response to receiving the input indicating the occurrence of the condition.

7. A method comprising:
   (a) storing, by a genetic material tracking platform, attributes associated with cryogenically stored genetic material deposits by, for each genetic material deposit of the cryogenically stored genetic material deposits:
      (i) storing, by the genetic material tracking platform, a private record on a database, wherein the private record includes a set of attributes for that genetic material deposit, and a current owner of that genetic material deposit;
      (ii) storing, by the genetic material tracking platform, an immutable record on a blockchain, wherein the immutable record includes a cryptographic hash that is based on a preceding immutable record, and a pointer that corresponds to the private record, wherein the pointer is usable to determine a correspondence between the private record and the immutable record;
      (iii) storing, by the genetic material tracking platform, one or more documentary records associated with that genetic material deposit, and storing a set of immutable documentary records on the blockchain based on the one or more documentary records;
   (b) providing, by the genetic material tracking platform, an online repository for displaying information regarding each of the genetic material deposits on an online interface;
   (c) receiving, by the genetic material tracking platform, search criteria entered by a user via the online interface;
   (d) determining, by the genetic material tracking platform, which of the genetic material deposits satisfy the search criteria;
   (e) identifying, by the genetic material tracking platform, via the online interface:
      (i) the genetic material deposits that satisfy the search criteria;
      (ii) a verification of the current owner for each of the genetic material deposits that satisfy the search criteria that is based on one or more private records from the database that are associated with that genetic material deposit and one or more immutable records from the blockchain that are associated with that genetic material deposit;
      (iii) the one or more documentary records for each of the genetic material deposits that satisfy the search criteria;
      (iv) a current location and any past locations of the genetic material deposits that satisfy the search criteria, based on a plurality of immutable location records from the blockchain; and
      (v) a verification of a plurality of cryptographic hashes from the blockchain, including the cryptographic hash for each of the genetic material deposits that satisfy the search criteria, cryptographic hashes for each of the one or more documentary records, and cryptographic hashes for each of the current location and any past locations.

8. The method of claim 7, wherein the cryogenically stored genetic material deposits comprise material deposits stored at a plurality of different facilities.

9. The method of claim 7, wherein the cryogenically stored genetic material deposits comprise embryos that are each associated with a female donor and a male donor.

10. The method of claim 9, wherein the search criteria comprises at least one attribute of the female donor or an attribute of the male donor, and wherein the genetic material deposits that satisfy the search criteria are identified based upon the set of attributes for each.

11. The method of claim 10, wherein the set of attributes includes one or more of an eye color, a hair color, a height, and a weight.

12. The method of claim 10, wherein the set of attributes includes a genetic attribute, a physiological attribute, a chronological attribute, and an attained attribute.

13. The method of claim 10, wherein at least one attribute of the set of attributes is an education level.

14. A method of genetic material provenance tracking, the method comprising:
   (a) receiving, by a genetic material tracking platform and via a mobile computing device, a vessel identifier from a computer readable identifier associated with a genetic material;
   (b) associating, by the genetic material tracking platform and in a database, the vessel identifier with a location;
   (c) subsequent to the collection of the genetic material from a donor, linking, by the genetic material tracking platform, the genetic material collected from the donor to a globally unique identifier of the donor by:
      (i) storing, by the genetic material tracking platform, a private record on a database, wherein the private record includes the vessel identifier and the globally unique identifier; and
      (ii) storing, by the genetic material tracking platform, an immutable record on a blockchain, wherein the immutable record includes a cryptographic hash that is based on a preceding immutable record, and a pointer that corresponds to the private record, wherein the pointer is usable to determine a correspondence between the private record and the immutable record;

(d) storing a first immutable location record on the blockchain that associates the vessel identifier with a first location identifier that describes the location;

(e) after the genetic material is moved from the location to a subsequent location, receiving, by the genetic material tracking platform, the vessel identifier and storing a second immutable location record on the blockchain that associates the vessel identifier with a second location identifier that describes the subsequent location, wherein each of the location and the subsequent location include an address of a facility, a storage area of the facility, and a section of the storage area;

(f) creating an audit log of the genetic material based on:
  (i) one or more private records from the database that are associated with the genetic material;
  (ii) one or more immutable records from the blockchain that are associated, by pointers, with the one or more private records, including a plurality of immutable location records that describe a current location and any past locations of the genetic material; and
  (iii) a verification of a plurality of cryptographic hashes from the blockchain, including the cryptographic hash and a set of cryptographic hashes associated with the plurality of immutable location records.

15. The method of claim 14, wherein the audit log provides an identity of the donor.

\* \* \* \* \*